United States Patent [19]

Rice

[11] Patent Number: 4,568,071
[45] Date of Patent: Feb. 4, 1986

[54] LINEAR X-RAY TABLE DRIVE

[75] Inventor: Paul G. Rice, Lincoln, Mass.

[73] Assignee: John K. Grady, Littleton, Mass.

[21] Appl. No.: 575,207

[22] Filed: Jan. 30, 1984

[51] Int. Cl.[4] ............................................. A61G 13/00
[52] U.S. Cl. .................................. 269/322; 378/209; 108/20; 108/143
[58] Field of Search ...................... 269/322; 378/209; 108/143, 137, 102, 20; 5/81 B

[56] References Cited

U.S. PATENT DOCUMENTS

| | | | |
|---|---|---|---|
| 3,158,742 | 11/1964 | Morel et al. | 378/209 |
| 3,463,921 | 8/1969 | Warden | 378/209 X |
| 3,797,411 | 8/1968 | Rossi | 378/209 X |
| 3,944,204 | 3/1976 | Cesar | 378/209 X |
| 4,131,802 | 12/1978 | Braden et al. | 269/322 X |
| 4,408,341 | 10/1983 | Christiansen | 378/209 X |
| 4,475,072 | 10/1984 | Schwehr | 378/209 X |

FOREIGN PATENT DOCUMENTS

| | | | |
|---|---|---|---|
| 1159891 | 7/1958 | France | 378/209 |
| 894500 | 4/1962 | United Kingdom | 378/209 |

Primary Examiner—Frederick R. Schmidt
Attorney, Agent, or Firm—James H. Grover

[57] ABSTRACT

A radiotransparent table for supporting a patient in an X-radiography zone slides in linear bearings on a standard. The table is motor driven through a cable or like linkage anchored at the head and foot of the table and passing over the motor drive roll and an idler roll located on the stand between the drive roll and zone so that substantially the full length of the table can be moved to the radiography zone. The head and foot anchors are unobstructed in movement toward the drive roll. Preferably there are two symmetrical sets of rolls, anchors and linkages at opposite sides of the table applying neutralizing torques to the table.

7 Claims, 3 Drawing Figures

4,568,071

LINEAR X-RAY TABLE DRIVE

BACKGROUND

In some dynamic X-radiography procedures such as peripheral angiography and venography it is necessary to support a human patient on a table and drive the table through the radiography zone of the X-ray beam so that the patient is radiologically examined nearly his full length from shoulders to ankles, but without moving the patient relatively to the table. Typically the patient receives an injection of radio-opaque dye at one point in his body and the progress of the head of the dye stream in veins up or down his body is recorded by a rapid succession of overlapping X-ray exposures. To insure that successive exposures overlap reasonably uniformly, a motorized or manual table drive mechanism is required. Metallic parts of the drive mechanism, being radio-opaque, must not extend into the radiography zone. On the other hand, because of space limitations in X-ray rooms the drive mechanism should not extend beyond the head or foot of the patient support table.

While pinion gear drive of a rack attached lengthwise under a patient table is satisfactory for some X-ray procedures, it does not meet the three above mentioned requirements firstly that the table travel nearly the full patient length, secondly that metallic parts of the drive be located outside the radiography zone, and thirdly that no drive parts extend beyond the head or foot ends of the patient table.

It is the object of the present invention to provide a radiographic support for a patient which meets the above three requirements.

SUMMARY OF THE INVENTION

According to the invention a radiographic support comprises a stand; a patient table having a head end and a foot end spaced apart a standard patient length; linear bearings mounting the table on the stand for endwise sliding travel of the table through a radiography zone passing through the stand and table; drive roll means on the stand; idler roll means on the stand between the drive roll means and zone; a foot anchor at the foot end of the table; a head anchor on the table spaced from the foot anchor toward the head end of the table; and flexible linkage fixed to the head and foot anchors and extending over the drive and idler roll means for causing travel of the table a greater distance than the spacing between anchors; whereby substantially the full length of the table can be driven through the radiography zone without extending the table drive means beyond the length of the table.

DRAWING

DESCRIPTION

Figure 1:
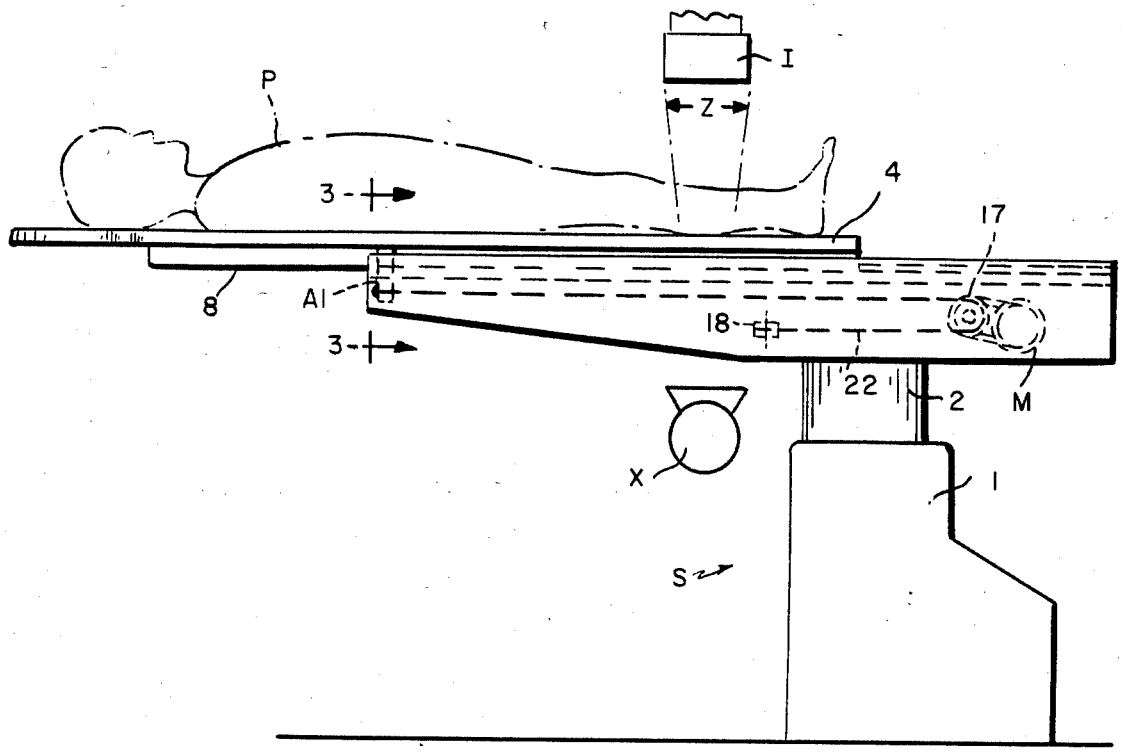
FIG. 1 is a side elevation of a radiographic support according to the invention.

The radiographic support of the figures comprises a base 1 enclosing a columnar ram 2 connected to a platform 3 which the ram can lift and rotate. The base 1, ram 2 and platform 3 constitute a stand for a patient table 4. The patient table is slidingly mounted on the stand and has a head end 6 and a foot end 7 spaced apart the height of a standard patient P, e.g. six feet and two inches, the 95th percentile of male height. The table 4 has at each side linear bearings 8 extending from the shoulder position of the table to the ankle position. These bearings ride on parallel rods 9 mounted on elongate bars 11 extending the length of the platform 3. The table can travel endwise on its bearings through a radiography zone Z in the beam radiated from an X-ray tube X to an image receptor I such as an image intensifier optically coupled to a fast action still camera for rapid recording of multiple successive X-ray exposures of the patient P.

Except for its linear bearings the table 4 is transparent to X-radiation. By linear bearings is meant any bearings guiding the table on linear travel. Similarly the radio-opaque portions of the base 1, column 2 and platform 3 comprising the stand for the table 4 are located outside the radiography zone Z, as is the drive mechanism for the table 4.

Illustrative of the invention, the table drive mechanism includes a drive shaft 16 driven by a motor M and turning two drive rolls 17 which may be pulleys or sprocket wheels rotatively mounted on the underside of the platform 3. Also rotatively mounted on the underside of the platform are idler rolls 18 located between the drive rolls and the radiography zone. Depending from the table 4 below the platform 3 to the level of the drive and idler rolls are a pair of head anchors A1 and A2 toward or at the head end of the table and a pair of foot anchors B1 and B2 at the foot end of the table. The head anchors are spaced from the foot anchors toward the head end of the table and spaced transversely of the table as are the idler rolls 18 so that the head anchors have unobstructed travel to the drive rolls, and the foot anchors have unobstructed travel to the idler rolls. Two flexible linkages 21 and 22, which may be cables, belts or chains for example, connect the anchors as follows. One linkage 21 is connected at its respective ends to one head anchor A1 and one foot anchor B1 passing over one drive roll and two idler rolls. All the anchors and rolls are exposed below the stand platform without obstruction of access to the linkages. The other linkage is connected at its ends to the other head and foot anchors and also passes over a second set of drive and idler rolls. Employing two sets each of drive rolls, idler rolls, head and foot anchors and linkages disposed in transverse symmetry on the table and stand is preferred because rotation of the drive rolls will result in application equal and opposite, i.e. neutralizing, torques at the anchors on the table so that the table will not be twisted when driven linearly.

Figure 2:
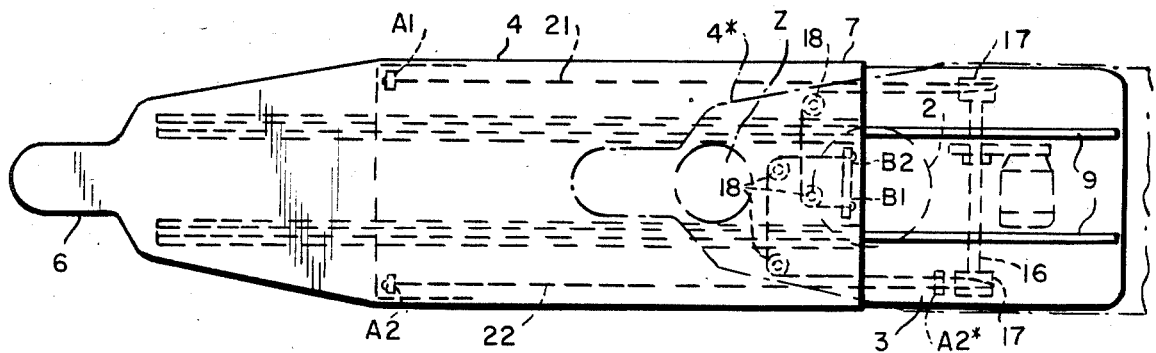
FIG. 2 is a plan view of the support.
Figure 3:
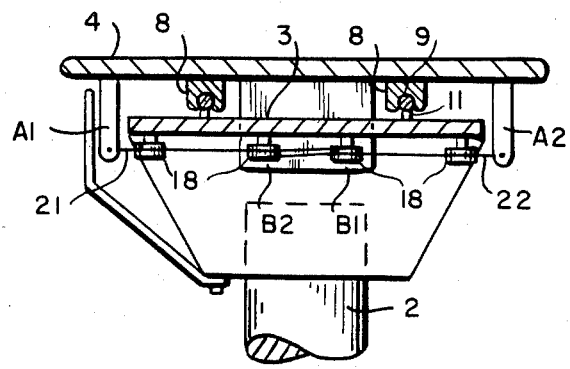
FIG. 3 is an endwise section of the support on lines 3—3 of FIG. 1.

When the drive rolls 17 are turned with the table in the position shown in solid lines in FIG. 2 the two linkages 21 and 22 pull on the head anchors A1 and A2 respectively while paying out at the foot anchors B1 and B2. The table 4 is thereby driven from the solid line position in which the foot end is in the radiography zone toward a phantom position 4* shown fragmentarily in FIG. 2. This travel of the table in the foot end direction to the right of FIG. 2 is limited by approach of the head anchor A2, e.g., to a position A2* at the drive roll shown in phantom lines in FIG. 2. Travel in the head end direction is limited by approach of the foot anchor B1 or B2 to the idler rolls as shown in dashed lines in FIG. 2. This travel is greater than the distance between anchors and moves the table substantially from head to foot through the radiography zone without requiring extension of the drive mechanism beyond the length of the table between head and foot ends.

I claim:

1. A radiographic support comprising:
a stand;
a patient table having a head end and a foot end spaced apart a standard patient length;
linear bearings mounting the table on the stand for endwise sliding travel of the table in two directions through a radiography zone passing through the stand and table;
drive roll means on the stand;
idler roll means on the stand between the drive roll means and zone;
a foot anchor at the foot end of the table;
a head anchor on the table spaced from the foot anchor toward the head end of the table; and
flexible linkage terminating at the head and foot anchors and extending over the drive and idler roll means, one anchor being connected by the linkage directly to the drive means so as to allow travel of the one anchor beyond the idler rolls in both directions of table travel with travel of the table being a greater distance than the spacing between anchors.

2. A support according to claim 1 wherein the table is radiotransparent in the radiography zone.

3. A support according to claim 1 wherein the support stand is radiotransparent in the radiography zone.

4. A support according to claim 1 wherein the head anchor has unobstructed travel to the drive roll means.

5. A support according to claim 1 wherein the foot anchor has unobstructed travel to the idler roll means.

6. A support according to claim 1 wherein there are two sets each of drive rolls, idler roll, head anchor, foot anchors and linkage, the elements of one set being disposed in transverse symmetry on the table and stand so as to apply neutralizing torques to the table.

7. A support according to claim 1 wherein the stand includes a platform beneath the table, and the anchors and roll means are exposed below the platform.

* * * * *